United States Patent [19]

Wu et al.

[11] 4,049,714
[45] Sept. 20, 1977

[54] N-PHENYL AMIDINES

[75] Inventors: Yao Hua Wu; Walter G. Lobeck, both of Evansville, Ind.

[73] Assignee: Mead Johnson & Company, Evansville, Ind.

[21] Appl. No.: 609,885

[22] Filed: Sept. 2, 1975

Related U.S. Application Data

[60] Division of Ser. No. 466,753, May 3, 1974, abandoned, which is a continuation-in-part of Ser. No. 255,701, May 22, 1972, Pat. No. 3,816,454, which is a continuation-in-part of Ser. No. 47,589, June 18, 1970, abandoned.

[51] Int. Cl.$^2$ .................................... C07C 123/00
[52] U.S. Cl. .......................... 260/564 R; 424/248.56; 260/343.7; 260/501.12; 260/501.14; 424/248.51; 424/280; 424/316
[58] Field of Search .......... 260/564 R, 343.7, 501.12, 260/501.14

[56] References Cited
PUBLICATIONS

Chemical Abstracts, vol. 31, 5774(a), (1937).
Chemical Abstracts, vol. 49, 10,227(a).
Chemical Abstracts, vol. 57, 14,975(b), (1962).

*Primary Examiner*—Gerald A. Schwartz
*Attorney, Agent, or Firm*—Robert H. Uloth; Robert E. Carnahan

[57] ABSTRACT

N-Phenyl amidines which have diuretic, antithrombogenic, smooth muscle relaxant, anti-inflammatory and antiarrhythmic properties have been discovered. They are prepared by reacting a substituted aniline with a carboxamide selected from the group consisting of amides and lactams in the presence of phosphorus oxychloride. Typical examples of substituted N-phenyl amidines thus obtained are 5-methyl-2-(N-phenylbenzylamino)-1-pyrroline, 2-(N-phenylbenzylamino)-1-pyrroline, 3-[(N-1-pyrrolin-2-yl-p-anisidino)methyl]indole and 4,5,6,7,8,9-hexahydro-2-(N-phenylphenethylamino)-3H-azonine. Indole substituted N-phenyl amidines can be rearranged to provide iminopyrrolinidinylindoles which are useful as diuretic, antithrombogenic and smooth muscle relaxant agents. In the case of 3-[(N-1-pyrrolin-2-yl-p-anisidino)methyl]indole, the rearranged product is 3-[[2-(p-methoxyphenylimino)-1-pyrrolindinyl]methyl]indole.

6 Claims, No Drawings

N-PHENYL AMIDINES

CROSS REFERENCE TO RELATED APPLICATIONS

This application is a division of application Ser. No. 466,753, filed May 3, 1974, and now abandoned, which is a continuation-in-part of copending application Ser. No. 255,701, filed May 22, 1972 and now U. S. Pat. No. 3,816,454, which is a continuation-in-part of then copending application Ser. No. 47,589 filed June 18, 1970, and now abandoned.

BACKGROUND OF THE INVENTION

A mew class of amidines having pharmaceutical properties is the subject of the present invention. Administration of these substances to mammals produces diuretic, antithrombogenic, smooth muscle relaxant, anti-inflammatory and antiarrhythmic effects therein.

Diuretics can be grouped according to their molecular structure into four general classifications. They are, in their chronological order of introduction as therapeutics, organomercurial compounds, carbonic anhydrase inhibitors, thiazides typified by 6-chloro-7-sulfamoyl-1,2,4-benzothiadiazine-1,1-dioxide (chlorothiazide), and a miscellaneous group of chemically unrelated compounds. Among the miscellaneous group of compounds are; 4-chloro-N-furfuryl-5-sulfamoylanthranilic acid (furosemide), 2,4,7-triamino-6-phenylpteridine (triamterine) and certain steroid compounds which are aldosterone antagonists. As a chemical class, the N-phenyl amidine of the present invention differ structurally from the aforementioned classes of diuretic agents.

The principal function of a diuretic is to reduce the volume of extracellular fluid in order to eliminate edema or prevent its development. Along with the enhancement of the urinary excretion of water, diuretics generally produce an elimination of electrolytes such as sodium, chloride, potassium, and bicarbonate ions. In many instances, as with the thiazides, there is a nonselective elimination of electrolytes and electrolyte imbalance results, particularly with respect to potassium depletion which leads to muscular weakness.

SUMMARY OF THE INVENTION

This invention relates to N-phenyl amidines of Formula I and non-toxic pharmaceutically acceptable acid addition salts thereof.

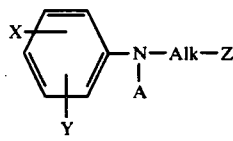

Formula I

These substances, which are characterized by Formula I, are new compositions of matter and are useful as diuretic agents in mammals. In addition, they are useful as antithrombogenic agents, smooth muscle relaxants, anti-inflammatory and antiarrhythmic agents.

In Formula I, Alk represents an alkylene radical containing 1 or 2 carbon atoms such as methylene (—CH$_2$—), ethylene (—CH$_2$CH$_2$—) and 1,1-ethylene

The X and Y substituents are independently selected from the group consisting of hydrogen, halogen, trifluoromethyl, lower alkoxy of from 1 to 4 carbon atoms inclusive, and lower alkyl of from 1 to 4 carbon atoms inclusive. Halogen subtituents include chlorine, bromine, fluorine, and iodine. By the term "independently selected" as used herein, it is meant that the X and Y substituents may or may not be identical.

Z is selected from the group consisting of phenyl, 2-thienyl, 2-furyl, and $R^4$ and $R^5$ substituted 3-indole represented by the formula

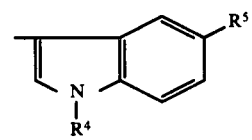

wherein $R^4$ is hydrogen, lower alkyl or benzyl and $R^5$ is hydrogen, halogen, preferably bromine, or lower alkoxy. A is a substituent selected from the group consisting of an imino moiety represented by:

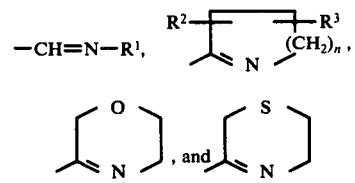

wherein $R^1$ is lower alkyl of from 1 to 4 carbon atoms inclusive, $n$ is an integer of 1 to 3 and $R^2$ and $R^3$ are independently selected from the group consisting of hydrogen and lower alkyl of from 1 to 4 carbon atoms inclusive. Among the "A substituents" which are represented by the symbol

are 1-pyrroline; 5-methyl-1-pyrroline; 5,5-dimethyl-1-pyrroline; 4-methyl-1-pyrroline; 3-methyl-1-pyrroline; 3,4,5,6-tetrahydro-2H-azepine; 3,4,5,6-tetrahydropyridine; 3,4,5,6,7,8-hexahydroazocine; 4,5,6,7,8,9-hexahydro-3H-azonine; 1-azacyclotridecene. It is to be understood that by the terms "lower alkyl" and "lower alkoxy" as used hereinabove, it is meant that the carbon chains which comprise these groups include both straight and branched chain carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

Illustrative of non-toxic pharmaceutically acceptable acid addition salts of N-phenyl amidines of Formula I are the salts of a variety of inorganic and organic acids such as sulfuric, phosphoric, hydrochloric, hydrobromic, hydroiodic, sulfamic, acetic, lactic, malic, succinic, maleic, fumaric, tartaric, citric, gluconic, glutaric, ascorbic, benzoic, cinnamic, and related acids.

A preferred group of N-phenylamidines of Formula I are those characterized by Formula Ia

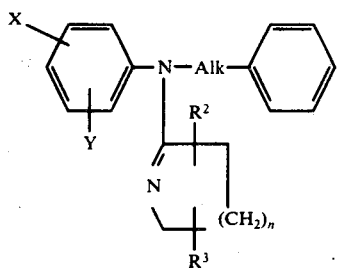

Formula Ia wherein the symbols "Alk, X, Y, $R^2$, $R^3$ and $n$" are as previously defined. The compounds of Formula Ia exhibit substantial antiarrhythmic activity in mammals apart from the pharmaceutical properties mentioned hereinabove. Specific compounds particularly preferred for their antiarrhythmic properties are:

3,4,5,6-tetrahydro-7-[(N-phenyl)phenethylamino]-2H-azepine, 3,4,5,6,7,8-hexahydro-2-(N-phenylphenethylamino)azocine, 4,5,6,7,8,9-hexahydro-2-(N-phenylphenethylamino)-3H-azonine.

According to the process of the present invention for the preparation of compounds of Formula I, a substituted aniline having the formula

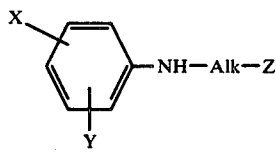

is reacted with a carboxamide selected from the group consisting of carboxamides of the formula

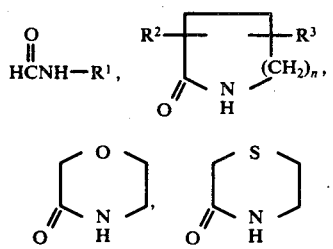

in the presence of phosphorus oxychloride in a suitable inert organic solvent. The symbols "Alk", "Z", "X", and "Y" in the substituted aniline reactant and "$R^1$", "$R^2$", "$R^3$", and "$n$" in the carboxamide reactant have the meanings hereinabove described for Formula I. Among the suitable carboxamide reactants are: N-alkylformamides such as N-methylformamide, N-isopropylformamide, N-tert.-butylformamide, N-butylformamide and the like. Cyclic carboxamides (lactams) can also be employed and include 2-pyrrolidinone, 5-methyl-2-pyrrolidinone, 5,5-dimethyl-2-pyrrolidinone, ε-caprolactam, δ-valerolactam, 3-ketothiomorpholine, 3-ketomorpholine, 4-methyl-2-pyrrolidinone, 3-methyl-2-pyrrolidinone, 2-azacyclononanone, 2-azacyclooctanone, 2-azacyclotridecanone.

In carrying out the process for the preparation of N-phenyl amidines of Formula I, approximately stoichiometric quantities of substituted aniline and appropriate carboxamide reactants and phosphorus oxychloride are mixed together in an inert aprotic solvent. A suitable and preferred solvent for carrying out the process is 1,2-dichloroethane. Other suitable solvents such as chloroform, carbon tetrachloride, 1,1-dichloroethane, benzene, toluene, hexane and the like may be satisfactorily employed. The mode of addition of the reactant is not critical in carrying out the process. For example, a solution or suspension of substituted aniline and a carboxamide in 1,2-dichloroethane can be added to a solution of phosphorus oxychloride or the sequence of addition may be reversed and a solution of phosphorus oxychloride can be added to a solution of the carboxamide and aniline. Alternatively, phosphorus oxychloride can be first added to the aniline reactant and the carboxamide reactant then added. Another suitable adaptation of the process is the combination of phosphorus oxychloride with a carboxamide and the addition of this mixture to the aniline reactant. Combination of the reactants provides an exothermic reaction and external cooling can be employed to moderate the reaction. However, this is not necessary for the successful completion of the reaction. The reaction of a carboxamide with the aniline takes place in a facile manner when the reactants are combined and generally does not require prolonged reaction for the formation of the N-phenyl amidine compounds of Formula I. We prefer to carry out the reaction by the addition of phosphorus oxychloride in one portion to the mixture of the aniline and carboxamide reactants in 1,2-dichloroethane. Although the reaction may be carried out at temperature of about $-35°$ C. to $100°$ C., it is generally preferred to carry out the combination of the reactants at room temperature with efficient stirring and to then stir the reaction mixture overnight before isolating the product.

Illustrative of the preferred method for the preparation of the compounds of Formula I is the addition of phosphorus oxychloride to a mixture of N-benzylaniline and 5-methyl-2-pyrrolidinone in 1,2-dichloroethylene which provides 5-methyl-2-(N-phenylbenzylamino)-1-pyrroline.

In the case of the N-phenylamidines of Formula I wherein Z is an indole, we have found that it is desirable to add an equimolar amount of a tertiary amine such as triethylamine in carrying out the hereinabove described process. The addition of triethylamine to the reaction mixture is not necessary for the successful completion of the reaction but is preferred in some instances in order to increase yields and obtain purer products.

The compounds of Formula I are stable in the form of their pharmaceutically acceptable acid addition salts, e.g., as their hydrochlorides. As free bases, however, compounds of Formula I wherein Z is $R^4$, $R^5$-indole, Alk is methylene and $R^4$ is hydrogen, rearrange in the presence of heat or in solvents such as ethanol at reflux temperature to provide products of the present invention characterized by Formula II

FORMULA II

-continued

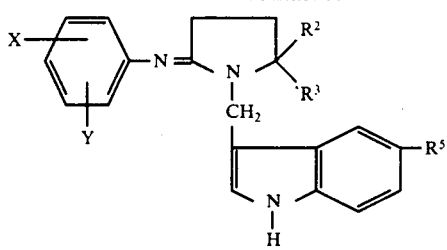

wherein X, Y, R², R³, and R⁵ are as described above. Non-toxic pharmaceutically acceptable acid addition salts of the rearranged products of Formula II can be prepared as described herein for the compounds of Formula I. It is to be understood that the compounds of Formula II are considered to be part of the present invention. The iminopyrrolidinylindoles of Formula II are active diuretic agents and have antithrombogenic and smooth muscle relaxant properties according to biological tests described herein.

Conversion of N-phenyl amidine free bases falling within general Formula I and the iminopyrrolinylindole free bases characterized by Formula II to corresponding non-toxic pharmaceutically acceptable acid addition salts is accomplished by admixture of the base with a selected acid in an inert organic solvent such as ethanol, benzene, ethyl acetate, ether, halogenated hydrocarbon and the like. One preferred method is to treat the N-phenyl amidine with substantially one chemical equivalent of ethanolic hydrogen chloride in ethanol solution and precipitate the salt therefrom by addition of anhydrous ether. The N-phenyl amidine salts of the present invention are generally water soluble whereas the bases are substantially insoluble in water.

The method hereinabove described for the preparation of the compounds of Formula I is a modification of a procedure described by H. Bredereck and K. Bredereck, Ber., 94, 2278-95 (1961); refer to C. A. 55: 27371. According to this reference, a carboxamide such as 2-pyrrolidinone is first treated with phosphorus oxychloride in benzene and then with aniline to provide the amidine "2-phenyliminopyrrolidine". This amidine is substantially inactive as a diuretic agent when tested according to the Lipschitz method discussed below.

The compounds of the present invention are evaluated as diuretics according to the method of W. L. Lipschitz, et al., J. Pharmacol. Expt. Therap., 79, 97 (1943). In this method, groups of 8 rats are fasted 18 hours prior to the experiment. A control group is hydrated orally with 25 ml. per kilogram of body weight of isotonic saline solution which is also the vehicle used for dosing the test compound. One control group received a dose of 960 mg./kg. of body weight of urea. Animals of other groups are treated with various doses of the test compound. Immediately after treatment, the animals are placed in metabolism cages (two rats of the same group per cage) and maintained without food or water for 5 hours. The volume of urine excreted by each pair is determined after this period and the pooled urine is analyzed for sodium, potassium, and chloride ions. The results for the test compounds are expressed as ratios of the volume of urine or total quantities of electrolytes (i.e., sodium, potassium, and chloride) excreted during the experimental period compared to the urea control group. In this test, the N-phenyl amidines of Formula I were orally administered in doses ranging from 2.7 to 25 mg./kg. of body weight.

In the Lipschitz test, the results obtained with the N-phenyl amidines of the present invention clearly indicate that they are orally effective diuretic agents. Substantially increased urine flow, sodium, and chloride ion excretion are obtained following oral administration of the N-phenyl amidines of Formula I.

One of the disadvantages associated with diuretics such as the thiazides is believed to stem largely from increased excretion of potassium ion concomitant with water elimination. This is overcome with the N-phenyl amidines of the present invention, whereby water elimination is obtained while a favorable balance of sodium to potassium ion excretion is maintained. For example, oral administration of a representative N-phenyl amidine of Formula I, 5-methyl-2-(N-phenylbenzylamino)-1-pyrroline hydrochloride to the rat at a dose of 6.25 mg./kg. of body weight when compared to the urea control group affords a ratio of 2.32 for volume excretion, 2.03 for sodium ion excretion and 0.75 for potassium ion excretion. Thus, the ratio of sodium ion excretion to potassium ion excretion is 2.03/0.75 which is equivalent to a value of 2.7. Hydrochlorothiazide, a well-known diuretic agent, at the same dosage has a ratio of sodium to potassium ion excretion of 1.65. As stated hereinabove, excessive excretion of potassium ion may cause an electrolyte imbalance resulting in adverse side effects.

The compounds of Formulas I and II exert their optimum therapeutic effects at doses ranging from 0.1 to 100 mg./kg. of body weight and, in particular, diuretic activity when orally administered to mammals in non-toxic doses ranging from about 0.1 to 25 mg./kg. of body weight per day. These substances may be also administered parenterally, but the oral route is preferred as a matter of convenience and ease of administration. Oral administration of the N-phenyl amidines to mice provides $ALD_{50}$ values in the range of 50 to 500 mg./kg.

In accord with the present invention, there is provided a therapeutic process which comprises administering to a mammal a compound of Formula I or Formula II in a effective dose of from about 0.1 to 100 mg./kg. of body weight of said mammal to produce an effect therein selected from the group consisting of diuretic, antithrombogenic, smooth muscle relaxant, antiinflammatory and antiarrhythmic effects.

The N-phenyl amidines of Formula I may be administered to mammals in the form of free bases or as one of their non-toxic pharmaceutically acceptable acid addition salts. In either form, they may be compounded and formulated with organic or inorganic solid materials or liquids which are pharmaceutically acceptable carriers to provide pharmaceutical compositions of unit dosage form. Preferably, the unit dosage form comprises a pharmaceutical carrier and the N-phenyl amidine in an amount ranging from about 0.1 to 100 mg./kg. of body weight of the mammal treated. An effective dose of the unit dosage form can then be administered to mammals to elicit diuresis. Pharmaceutical compositions considered within the scope of this invention may take the form of tablets, powder, granules, capsules, suspensions, solutions, and the like. Suitable pharmaceutical carriers comprise both solids and liquids such as corn starch, lactose, calcium phosphate, stearic acid, polyethylene glycol, water, sesame seed oil, peanut oil, propylene glycol, and so forth.

Evaluation of the compounds of the present invention for antithrombogenic activity is carried out according to a method described by Born, Nature, 194, 927 (1962) and O'Brien, J. Clin. Path., 15, 446 (1962). This is essentially a nephelometric method in which the change in turbidity of a specimen of platelet rich blood plasma is measured on causation of platelet aggregation by addition of a thrombogenic inducing agent such as adenosine diphosphate, epinephrine, or collagen. The compounds of the present invention are effective antithrombogenic agents according to this test at concentrations in the order of about 30 to 100 mcg./ml.

Smooth muscle relaxant activity of the compounds of the present invention can be measured in standard in vitro and in vivo pharmacological tests. One such in vitro test is carried out essentially as follows. A segment of rabbit ileum is suspended and oxygenated in Tyrode's solution and affixed to a tension transducer for electronic recording of isometric contractions. After controlled responses to a standard dose of a spasmogen such as barium chloride (0.25 mg./ml.), acetyl choline chloride (1.0 mcg./ml.), etc., are established, the test compound is added and the response to the spasmogen, in the presence of the test agent, again determined. Test compound effect is measured as the percentage reduction in the response to the spasmogen, in the presence of the test compound, from the mean control response. A minimum of four trials is obtained with each of two to five different concentrations of the test compound. The data are expressed in log dose response curves and estimates made therefrom of the $EC_{50}$ (concentration causing 50% reduction in response of the tissue to the spasmogen). In general, the effect of compounds identified by Formula I on the rabbit ileum is similar to papaverine, a well-known smooth muscle relaxant. As might be expected, certain of the compounds are more active than others. For example, 3-[[N-(5-methyl-1-pyrrolin-2-yl)anilino]methyl] indole hydrochloride is 1.4 times more potent than papaverine while 3-[[N-(1-pyrrolin-2-yl)anilino]methyl]indole hydrochloride is from 0.5 to about 0.8 as potent as papaverine. Other compounds of particular interest are N-benzyl-N'-tert.-butyl-N-phenylformamidine hydrochloride and N'-tert.-butyl-N-phenethyl-N-phenylformamidine hydrochloride which compared to papaverine are 6 to 16 and 5 times as potent respectively.

Another in vitro test measuring the smooth muscle relaxant properties of the compounds of the present invention employs the guinea pig isolated tracheal spiral and is carried out essentially as described by Lish, et al., J. Pharmacol. Exp. Therap., 129, 191 (1960). As illustrative of the activity of the compounds of the present invention in this test there can be mentioned 3-[(N-1-pyrrolin-2-yl-p-anisidino)methyl]indole hydrochloride which is about 1.7 times as potent as aminophylline.

Smooth muscle relaxant properties of the compounds of the present invention can be demonstrated in vivo in the dog. In this test a dog is anesthetized with pentorbarbital-sodium and routinely arranged for recording of intestinal smooth muscle activity. (Goodman and Gilman, The Pharmacological Basis of Therapeutics, 2nd ed., The McMillan Co., 1960, New York). Intravenous administration of the compounds of the present invention identified by Formula I and Formula II generally produce marked intestinal smooth muscle relaxant at doses ranging from 1 to 10 mg./kg. body weight.

Intestinal smooth muscle relaxant activity can also be measured in an in vivo cat preparation. In this test, a balloon is inserted through a small incision in the stomach of an anesthetized cat to a point about 10 cm. down the duodenum and intralumenal intestinal pressure changes recorded. A solution or suspension of the test agent is administered intraduodenally about 2 cm. beyond the balloon placed for recording intraduodenal pressure in volume doses of 1 ml./kg. body weight. This means of administration mimics oral administration. Various doses of the test agent are administered and an inhibitory dose which supresses intestinal relaxation by 50% of maximum is determined. This value is designated the $ID_{50}$. N-benzyl-N'-tert-butyl-N-phenylforamidine hydrochloride compared to papaverine is about 1.5 times as potent in this test.

As a bronchodilating agent, 3-[(N-1-pyrrolin-2-yl-p-anisidino)methyl]indole hydrochloride is of particular interest. In the histamine challenged guinea pig aerosol test, refer to Turner, *Screening Methods In Pharmacology*, page 214 (1965) (Academic Press, New York), this compound is about 1.4 times as potent as aminophylline when administered orally.

The compounds of Formula I exhibit anti-inflammatory activity as demonstrated by the ability to inhibit formation of the local edema which forms on plantar injection of carrageenin into the foot of a rat. This test is performed on adult rats of either sex using a group of ten animals as a non-medicated control and another group of ten which is treated orally with the test compound 15 min. prior to the induction of edema. Edema is induced by the plantar injection of 0.1 ml. of 0.5% solution of carrageenin to the right hind foot. The left hind foot is treated similarly with 0.1 ml. of 0.9% saline. Four hours later the volume of each hind foot is determined plethysmographically by measuring the volume of mercury displaced. The amount of edema is expressed as a percent increase in volume of the carrageenin-injected foot over the saline-injected foot. The percent inhibition of edema is calculated by dividing the mean percent increase in the edema of the carrageenin feet of the medicated group by the mean increase in the non-medicated group multiplied by 100. At a dose of 100 mg./kg of body weight, the compounds of Formula I generally produce from about 40 to 60% inhibition of edema.

The antiarrhythmic effects of the N-phenylamidines of Formula Ia may be demonstrated in standard in vitro and in vivo pharmacological tests such as the isolated rabbit atrium and dog arrhythmia.

In the in vivo dog arrhythmia test, the chest of an anesthetized dog is opened in the mid-line and the right and left atrial appendages exposed to small slits in the pericardium. Bypolar recording electrodes are affixed to atrial surfaces and a 4 × 4 mm. piece of clean cloth is fixed to surface of the right auricular appendage. Control recordings are made of various heart functions including femoral arterial blood pressure and right and left atrial electrograms. Atrial arrhythmia is then induced by placing 3–5 drops of a solution of aconitine on the cloth which is fixed to the right atrium. An irregular, rapid atrial rate is produced within 1 minute. Throughout the test, fresh aconitine (2–3 drops) is placed on the cloth at 10 minute intervals. The test compound is administered intravenously 5 minutes after the initial establishment of the arrhythmia and infusion continued at a slow rate until an effective dose which re-establishes normal rhythm of the heart is obtained.

The Formula Ia N-phenylamidines are effective both orally and parenterally as antiarrhythmic agents. For instance, intravenous administration of about 2.5 mg./kg. of 3,4,5,6-tetrahydro-7-[(N-phenyl)phenethylamino]-2H-azepine or 4,5,6,7,8,9-hexahydro-2-(N-phenylphenethylamino)-3H-azonine effectively restores normal cardiac rhythm to induced arrhythmia in the dog. A well known antiarrhythmia agent such as quindine administered in the same manner had an effective dose of 6.0 mg./kg.

Another in vivo test indicative of antiarrhythmic activity is chloroform induced arrhythmia in the mouse. Intraperitoneal administration of 3,4,5,6-tetrahydro-7-[(N-phenyl)phenethylamino]-2H-azepine prevents chloroform induced arrhythmia in the mouse at an $ED_{50}$ of 11.5 mg./kg. body weight.

In the rabbit atrium test, the left atrium is placed in Chenoweth's solution warmed to 30° C. and irrigated with 95% oxygen:5% carbon dioxide. The lower end of the atrium is attached to a small hook fixed in the bath and the upper end is connected to a transducer to record contractile activity. The atrium is electrically stimulated at a basic rate of 30 per minute employing square wave pulses of 10 millisecond duration at 1.2–1.5 times threshold voltage. The test compound is introduced into the bath and the test repeated after a 5 minute interval. A dose response relationship is obtained by additional doses of the test compound. Potency of a test agent can be expressed as the effective concentration which produces 50% of the maximal increase in the measured refractory period of the steady state atrium. This value is designated the $EC_{50}$. The $EC_{50}$ values for 3,4,5,6-tetrahydro-7-[(N-phenyl)phenethylamino]-2H-azepine hydrochloride, 3,4,5,6,7,8-hexahydro-2-(N-phenylphenethylamino)azocine hydrochloride hemihdrate and 4,5,6,7,8,9-hexahydro-2-(N-phenylphenethylamino)-3-H-azonine hydrochloride are respectively 7.2, 2.5 and 1.9 mcg./ml. Quinidine has an $EC_{50}$ of 18.0 mcg./ml.

The following examples illustrate the best mode contemplated for carrying out the present invention. They are merely illustrative and are not to be construed as limiting the scope of the claims in any manner whatsoever.

EXAMPLES 1–21 General procedure for the preparation of

N-phenyl amidines

Phosphorus oxychloride (0.1 mole) is added in one portion to a stirred mixture of an N-substituted aniline (0.1 mole) and the appropriate carboxamide (0.1 mole) in 150 ml. of 1,2-dichloroethane. After stirring the reaction mixture for a 16 hr. period, it is poured into crushed ice and 100 ml. of 20% sodium hydroxide. The dichloroethane layer is separated and extracted with 100 ml. of 1.5N hydrochloric acid and then with 100 ml. of water. The acidic aqueous portion is made basic with 20% sodium hydroxide solution providing an oil which is taken up in ether. The ethereal extract is dried over magnesium sulfate and then concentrated to provide the N-phenyl amidine product which is purified by distillation through a "short path" (ca., 10 cm.) column at reduced pressures.

The N-phenyl amidine free base is converted to the hydrochloride salt by dissolving in ethanol, acidifying the ethanolic solution with ethanolic hydrogen chloride and adding anhydrous ether unitl the hydrochloride salt precipitates from the solution.

Representative N-phenyl amidines prepared according to the hereinabove described procedures are enumerated in Table I. Table II reports analytical values and major infrared absorption peaks of the N-phenyl amidine products listed in Table I.

TABLE I

| | | N-PHENYL AMIDINES | | | |
|---|---|---|---|---|---|
| Ex. No. | Anilino Amidine Product | Reactants Amine | Reactants Carboxamide | Base B.P. ° C./mm Hg. | HCl Salt M.P. ° C. (comp.) |
| 1 | N'-tert-Butyl-N-phenethyl-N-phenylformamide hydrochloride | N-phenylphenethylamine | N-tert-butylformamide | 130–135/0.2 $n_D^{26}$ 1.5590 | 166.5–168 |
| 2 | N-Benzyl-N'-tert.-butyl-N-phenylformamidine hydrochloride | N-phenylbenzylamine | N-tert-butylformamide | 135–137/0.2 $n_D^{25}$ 1.5713 | 158.5–160 |
| 3 | N'-Isopropyl-N-phenyl-N-(1-phenylethyl)formamidine | N-phenyl-1-phenylethylamine | N-isoproylformamide | 105–108/0.15 $n_D^{26.5}$ 1.56500 | — |
| 4 | 2-(N-Phenylbenzylamin)-1-pyrroline hydrochloride | N-phenylbenzylamine | 2-pyrrolidinone | 151–153/0.2 $n_D^{25}$ 1.5976 | 133–135 |
| 5 | 5-Methyl-2-(N-phenylbenzylamino)-1-pyrroline hydrochloride | N-phenylbenzylamine | 5-methyl-2-pyrrolidinone | 135–140/0.2 $n_D^{25}$ 1.5830 | 173–175 |
| 6 | 5,5-Dimethyl-2-(N-phenylbenzylamio)-1-pyrroline hydrochloride | N-phenylbenzylamie | 5,5-dimethyl-2-pyrrolidinone | 124–130/0.1 m.p. 60–62° C. | 236.5–237.5 |
| 7 | 2-(N-Phenylphenethylamin)-1-pyrroline hydrochloride | N-phenylphenethylamine | 2-pyrrolidinone | 130–143/0.15 $n_D^{25.5}$ 1.5869 | 200.5–201.5 |
| 8 | 5-Methyl-2-)phenylphenethylamino)-1-pyrroline hydroochloride | N-phenylphenethylamine | 5-methyl-2-pyrrolidinone | 145–154/0.2 $n_D^{26}$ 1.5742 | 225–226 |
| 9 | 5,5-Dimethyl-2-(N-phenylphenethylamino)-1-pyrroline hydrochloride | N-phenylphenethylamine | 5,5-dimethyl-2-pyrrolidinone | 143–149/0.15 nhd $D^{26}$ 1.5622 | 192.5–194.5 |
| 10 | 3,4,5,6-Tetrahydro-7-[(N-phenyl)-phenethylamino]-2H-azepine hydrochloride | N-phenylethylamine | ε-caprolactam | 145–150/0.2 $n_D^{26}$ 1.5812 | 208.5–209.5 |
| 11 | 3,4,5,6-Tetrahydro-2-(N-phenylbenzylamino)pyridine hydrochloride | N-phenylbenzylamine | δ-valerolactam | 143–145/0.1 $n_D^{25}$ 1.5959 | 182.5–184.5 |
| 12 | 3,4,5,6-Tetrahydro-7-(N-phenylbenzylamino)-2H-azepine hydrochloride | N-phenylbenzylamine | ε-caprolactam | 146–149/0.1 $n_D^{25}$ 1.5900 | 194–196 |
| 13 | 5,6-Dihydro-3-(N-phenylbenzylamino)-2H-1,4-thiazine hydrochloride | N-phenylbenzylamine | 3-ketothiomorpholine | 155–1160/0.15 $n_D^{25}$ 1.6300 | 216–217.5 |
| 14 | 2-[N-(m-Trifluoromethylphenyl))benzylamino]-1-pyrroline hydrochloride | N-(m-trifloromethyl)phenyl)benzlamine | 2-pyrrolidinone | 135–140/0.15 $n_D^{25}$ 1.5480 | 174–175.5 |
| 15 | 2-[N-(o-Methoxyphenyl)benzylamino]-1-pyrroline hydrochloride | N-(o-methoxyphenyl)benzlamine | 2-pyrrolidinone | 150–155/0.15 $n_D^{25}$ 1.5898 | 176–178.5 |
| 16 | 2-[N-(3,4-Dichlorophenyl)benzylamino]-1-pyrroline hydrochloride | N-benzyl-3,4-dichloroaniline/ | 2-pyrrolidinone $n_D^{24}$ 1.6158 | 180–185/0.2 | 198–201 |
| 17 | 5-Methyl-2-[N-(m-trifluoromethylphenyl)benzylamino]-1-pyrroline hydrochloride | N-(m-trifloromethylphenyl)benzyalmine | 6-methyl-2-pyrrolidinone | 140–145/0.2 $n_D^{24}$ 1.5382 | 174.5–176.0 |
| 18 | 2-[3,4-Dichloro-N-(2-thenyl)anilino]-5-methyl-1-pyrroline hydrochloride | 3,4-dichloro-N-thenylaniline | 5-methyl-2-pyrrolidionone | 147–151/0.1 $n_D^{25}$ 1.6108 | 198–199 |

TABLE I-continued

N-PHENYL AMIDINES

| Ex. No. | Anilino Amidine Product | Reactants Amine | Carboxamide | Base B.P. ° C./mm Hg. | HCl Salt M.P. ° C. (comp.) |
|---|---|---|---|---|---|
| 19 | 5,5-Dimethyl-2-[N-(m-trifluoromethyl-phenyl)benzylamino]-1-pyrroline hydrochloride | N-(m-trifloromethyl-phenyl)benzyl-amine | 5,5-dimethyl-2-pyrrolidinone | 140–145/0.2 $n_D^{25}$ 1.5268 | 211.0–214.5 (corr. m.p.) |
| 20 | 2-(3-Chloro-N-furfurylanilino)-5,5-dimethyl-1-pyrroline hydrochloride | N-(furfuryl)-3-chloroaniline | 5,5-dimethyl-2-pyrrolidinone | 115–125/0.3 $n_D^{27}$ 1.5586 | 171.5–177 |
| 21 | 3-(3-Chloro-N-furfurylanilino)-5,6-dihydro-2H-1,4-oxazine hydrochloride | N-(furfuryl)-3-chloroaniline | 3-ketomorpholine | 135–145/0.15 $n_D^{27}$ 1.5840 | 154–155 |

TABLE II

ANALYSIS AND INFRARED ABSORPTION OF N-PHENYL AMIDINES

| Example Number | Anilino Amidine Product | | Analysis Calcd. | | Found | Infrared Absorption (0.5% KBr cm$^{-1}$) |
|---|---|---|---|---|---|---|
| 1 | N'-tert-Butyl-N-phenethyl-N-phenylformamidine | C | 72.02 | C | 71.83 | 3020; 2960; 1680; 1590; 1500; |
|  |  | H | 7.95 | H | 7.85 | 1380; 1190; 780; 705 |
|  |  | N | 8.84 | N | 8.75 |  |
| 2 | N-Benzyl-N'-tert.-butyl-N-phenylformamidine hydrochloride | C | 71.39 | C | 71.37 | 3030; 2960; 1690; 1500; 1490; |
|  |  | H | 7.65 | H | 7.80 | 1200; 770; 700 |
|  |  | N | 9.25 | N | 9.36 |  |
| 3 | N'-Ispropyl-N-phenyl-N-(1-phenyl-ethyl)formamidine | C | 81.75 | C | 80.93 | 2950; 1650; 1590; 1490; 1270; |
|  |  | H | 8.33 | H | 8.35 | 760; 690 |
|  |  | N | 10.52 | N | 10.41 |  |
| 4 | 2-(N-Phenylbenzylamino)-1-pyrroline hydrochloride | C | 71.19 | C | 69.91 | 3020; 1670; 1610; 1510; 1320; |
|  |  | H | 6.68 | H | 6.75 | 1220; 800; 720 |
|  |  | N | 9.77 | N | 9.63 |  |
| 5 | 5-Methyl-2-(N-phenylbenzylamino)-1-pyrroline hydrochloride | C | 71.86 | C | 71.74 | 3000; 1665; 1595; 1500; 1460; |
|  |  | H | 7.04 | H | 6.90 | 1290; 1220; 1080; 710 |
|  |  | N | 9.31 | N | 9.32 |  |
| 6 | 5,5-Dimethyl-2-(N-phenylbenzylamino)-1-pyrroline hydrochloride | C | 72.48 | C | 72.26 | 2860; 2800; 1650; 1580; 1450; |
|  |  | H | 7.36 | H | 7.39 | 1410; 1205; 1170; 780; 705 |
| 7 | 2-(N-Phenylphenethylamino)-1-pyrroline hydrochloride | C | 71.86 | C | 71.81 | 2860; 1670; 1590; 1500; 1315; |
|  |  | H | 7.04 | H | 7.15 | 1060; 755; 710 |
|  |  | N | 9.31 | N | 9.29 |  |
| 8 | 5-Methyl-2-(phenylphenethylamino)-1-pyrroline hydrochloride | C | 72.48 | C | 72.32 | 2860; 1660; 1580; 1490; 1305; |
|  |  | H | 7.36 | H | 7.36 | 1070; 760; 700 |
| 9 | 5,5-Dimethyl-2-(N-phenylphenethylamino)-1-pyrroline hydrochloride | C | 73.04 | C | 73.20 | 3000; 1650; 1580; 1490; 1450; |
|  |  | H | 7.66 | H | 7.75 | 1220; 1165; 750; 700 |
| 10 | 3,4,5,6-Tetrahydro-7-[(N-phenyl)phenethylamio]-2H-azepine hydrochloride | C | 73.04 | C | 72.86 | 3030; 2930; 1640; 1590; 1490; |
|  |  | H | 7.66 | H | 7.56 | 1450; 755; 705 |
|  |  | N | 8.52 | N | 8.49 |  |
| 11 | 3,4,5,6-Tetrahydro-2-(N-phenylbenzylamino)-pyridine hydrochloride | C | 71.86 | C | 71.92 | 3020; 2940; 1640; 1585; 1490; |
|  |  | H | 7.04 | H | 7.15 | 1450; 1350; 700 |
| 12 | 3,4,5,6-Tetrahydro-7-(N-phenylbenzylamino)-2H-azepine hydrochloride | C | 72.48 | C | 72.50 | 3000; 2925; 1630; 1580; 1490; |
|  |  | H | 7.36 | H | 7.48 | 1450; 790; 705 |
|  |  | N | 8.90 | N | 8.94 |  |
| 13 | 5,6-Dihydro-3-(N-phenylbenzylamino)-2H-1,4-thiazine hydrochloride | C | 64.03 | C | 64.00 | 2950; 1640; 1600; 1500; 1460; |
|  |  | H | 6.01 | H | 6.10 | 1210; 740; 710 |
| 14 | 2-[N-(m-Trifluoromethylphenyl)benzylamino]-1-pyrroline hydrochloride | C | 60.93 | C | 61.22 | 3020; 1675; 1455; 1330; 1190; |
|  |  | H | 5.11 | H | 4.94 | 1120; 715 |
|  |  | N | 7.90 | N | 7.98 |  |
| 15 | 2-[N-(o-Methoxyphenyl)benzlamino]-1-pyrroline hydrochloride | C | 68.24 | C | 68.00 | 2930; 1660; 1510; 1305; 1030; |
|  |  | H | 6.68 | H | 6.71 | 750; 705 |
|  |  | N | 8.84 | N | 8.76 |  |
| 16 | 2-[N-(3,4-Dichlorophenyl)benzylamino]-1-pyrroline hydrochloride | C | 57.40 | C | 57.11 | 3000; 1665; 1480; 1325; 1135; |
|  |  | H | 4.82 | H | 4.85 | 1040; 710 |
|  |  | N | 7.88 | N | 7.97 |  |
| 17 | 5-Methyl-2-]N-(m-trifluoromethylphenyl)benzyl-amino]-1-pyrroline hydrochloride | C | 61.87 | C | 61.69 | 3020; 1670; 1455; 1330; 1125; |
|  |  | H | 5.47 | H | 5.41 | 770: 715 |
|  |  | N | 7.60 | N | 7.49 |  |
| 18 | 2-[3,4-Dichloro-N-(2-thenyl)anilino]-5-methyl-1-pyrroline hydrochoride | C | 51.14 | C | 51.01 | 2980; 1655; 1475; 1305; 1135; |
|  |  | H | 4.56 | H | 4.37 | 1040; 710 |
|  |  | N | 7.45 | N | 7.45 |  |
| 19 | 5,5-Dimethyl-2-[N-(m-trifluoromethylphenyl)-benzylamino]-1-pyrroline hydrochloride | C | 62.74 | C | 62.64 | 2960; 1660; 1470; 1330; 1175; |
|  |  | H | 5.79 | H | 5.85 | 1135; 720 |
|  |  | N | 7.32 | N | 7.23 |  |
| 20 | 2-(3-Chloro-N-furfurylanilino)-5,5-dimethyl-1-pyrroline hydrochloride | C | 60.18 | C | 60.27 | 2990; 1665; 1595;1480; 1355; |
|  |  | H | 5.95 | H | 5.91 | 770 |
| 21 | 3-(3-Chloro-N-furfurylanilino)-5,6-dihydro-2H-1,4-oxazine hydrochloride | C | 55.06 | C | 55.14 | 3000; 11660; 1590; 1490; 1355; |
|  |  | H | 4.93 | H | 5.00 | 1140; 760; 705 |
|  |  | N | 8.56 | N | 8.46 |  |

EXAMPLES 22–31

Additional exemplification of N-phenyl amidines of the present invention are listed in Table III. They are prepared according to the general procedure hereinabove described in Example 1 by the reaction of the indicated substituted aniline and carboxamide reactants employing phosphorus oxychloride.

TABLE III
ADDITIONAL N-PHENYL AMIDINES

Structure: X and Y substituents on phenyl ring connected to N(A)-CH₂-phenyl

| Example Number | Product X | Y | A | Reactants |
|---|---|---|---|---|
| 22 | H | H | 4-methylpyrrolin-2-yl (CH₃ at 4-position) | N-Phenylbenzylamine and 4-methyl-2-pyrrolidinone |
| 23 | o-CH₃ | H | 3-methylpyrrolin-2-yl | N-(o-Tolyl)benzylamine and 3-methyl-2-pyrrolidinone |
| 24 | p-(CH₃)₃C | H | 5-methylpyrrolin-2-yl | N-(p-tert.-Butylphenyl)-benzylamine and 5-methyl-2-pyrrolidinone |
| 25 | m-CH₃ | p-CH₃ | 3-ketomorpholin-2-yl | N-(3,4-Dimethylphenyl)-benzylamine and 3-ketomorpholine |
| 26 | o-CH₃ | p-CH₃ | 3-ketothiomorpholin-2-yl | N-(2,4-Dimethylphenyl)-benzylamine and 3-ketothiomorpholine |
| 27 | H | H | —CH=N—CH₃ | N-Phenylbenzylamine and N-methylformamide |
| 28 | p-(CH₃)₃CO | H | 5-methylpyrrolin-2-yl | N-(p-tert.-Butoxyphenyl)-benzylamine and 5-methyl-2-pyrrolidinone |
| 29 | m-CH₃O | p-CH₃O | 5,5-dimethylpyrrolin-2-yl | N-(3,4-Dimethoxyphenyl)-benzylamine and 5,5-dimethyl-2-pyrrolidinone |
| 30 | H | H | 5,5-di(n-butyl)pyrrolin-2-yl | N-Phenylbenzlamine and 5,5-di(n-butyl)-2-pyrrolidinone |
| 31 | H | H | 5-n-butylpyrrolin-2-yl | N-Phenylbenzylamine and 5-n-butyl-2-pyrrolidinone |

EXAMPLE 32 Tablets.

The N-phenyl amidines of the present invention are compounded into tablets according to the following example.

| Material | Amount |
|---|---|
| 5-methyl-2-(N-phenylbenzylamino)-1-pyrroline hydrochloride | 56.8 g. |
| Magnesium stearate | 1.3 g. |
| Corn Starch | 12.4 g. |
| Corn Starch pregelatinized | 1.3 g. |
| Lactose | 188.2 g. |

The foregoing materials are blended in a twin-shell blender and then granulated and pressed into tablets weighing 250 mg. each. Each tablet contains 56.8 mg. of 5-methyl-2-(N-phenylbenzylamino)-1-pyrroline hydrochloride or 50 milligrams of the biologically active base.

EXAMPLE 33. Capsules

Hard gelatin capsules were filled with a mixture consisting of 80 g. of 5-methyl-2-(N-phenylbenzylamino)-1-pyrroline hydrochloride and 120 g. of corn starch so that each capsule contains 50 milligrams of the biologically active base, 5-methyl-2-(N-phenylbenzylamino)-1-pyrroline.

EXAMPLE 34.

3-[(N-1-Pyrrolin-2-yl-p-anisidino)methyl]indole hydrochloride

Phosphorus oxychloride (1.53 g., 0.01 mole) is added in one portion to a stirred mixture of 3-(p-anisidinomethyl)indole (2.52 g., 0.01 mole), 2-pyrrolidinone (0.85 g., 0.01 mole) and triethylamine (1.01 g., 0.01 mole) in 30 ml. of 1,2-dichloroethane. After stirring the reaction mixture for a 3 hr. period, it is poured into a mixture of crushed ice and 50 ml of 10% sodium hydroxide. The dichloroethane layer is separated and extracted with 100 ml. of 0.75 N hydrochloric acid. The acidic aqueous is extracted first with ether, made basic with 20% sodium hydroxide, and then extracted with ether. After drying over magnesium sulfate, the ethereal extract is concentrated to provide 1.3 g. of residue which crystallized from ethanol yields a basic substance melting at 135°–138° C.

A 7.1 g. sample of material obtained according to the hereinabove described procedure is taken up in ethanol and acidified with ethanolic hydrogen chloride to provide a hydrochloride salt. The ethanol solvent is removed under vacuum and the residue thus obtained suspended in benzene and slowly refluxed permitting the benzene mixture to distill therefrom. Distillatin is continued for a period of from 4 to 5 hr. during which time additional benzene is added as needed. This provides 7.13 g. of hydrochloride salt melting at 165°–175° C. This fraction is further purified by first triturating with hot acetone and then crystalizing the acetone insoluble product from isopropanol-ether. On standing, the acetone mother liquors provide additional product which is also crystallized from isopropanol-ether. The isopropanol-ether crystallized fractions are combined and recrystallized from ethanol-ether to yield 1.23 g. of analytically pure 3-[(N-1-pyrrolin-2-yl-p-anisidino)methyl]indole hydrochloride as a white solid, m.p. 176°–177° C. (corr.).

Analysis. Calc'd. for $C_{20}H_{21}N_3 \cdot HCl$ (percent): C,67.50; H,6.23; N,11.81; Cl,9.96. Found (percent): C,67.73; H,6.03; N,11.64; Cl,9.96.

Infrared (0.5% KBr Cm$^{-1}$): 3160, 1660, 1510, 1310, 1260, 1040, 850, 750.

NMR $\delta$ (ppm) (CDCl$_3$, tetramethylsilane ref.): 3.78 (s,3H), 5.31 (s,2H), 3.94 (m,2H). (D$_2$O, HDO-4.70 ppm. ref.): 3.52 (s,3H); 4.80 (s,2H); 3.57 (m,2H).

EXAMPLE 35

3-[[N-(1-pyrrolin-2-yl)anilino]methyl]indole hydrochloride

Phosphorus oxychloride (7.67 g., 0.05 mole) is added in one portion to a stirred mixture of 3-(anilinomethyl)indole (11.1 g., 0.05 mole), 2-pyrrolidinone (4.26 g., 0.05 mole) and triethylamine (5.06 g., 0.05 mole) in 100 ml. of 1,2-dichloroethane at ice bath temperature. Stirring is continued at that temperature for 15 min. and then at room temperature for about 16 hr. After quenching in crushed ice and aqueous sodium hydroxide, the reaction mixture is filtered providing 2.5 g., of solid free base m.p. 115°–117° C. The filtrate is worked up according to the method of Example 34 by extracting the dichloroethane layer with hydrochloric acid and subsequently extracting the acid extract with ether and then making basic with sodium hydroxide. Ether extraction of the basic aqueous mixture with ether and concentrating the dried ethereal extract affords a second free base fraction, 4.1 g., melting at 118°–120° C. The free base fractions are combined and a 5.1 g. sample converted to the hydrochloride salt in ethanol by treatment with ethanolic hydrogen chloride. Concentration of the acidic ethanolic solution provides a residue which is taken up in water and filtered from a small amount of solid. The filtrate is cooled and made basic with 10% aqueous sodium hydroxide affording the free base which is collected, 3.1 g., m.p. 118°–120° C. The repre- pared free base is then converted to the hydrochloride salt in the usual manner in ethanol by treatment with ethanolic hydrogen chloride. Addition of ether to the ethanolic solution yields analytically pure 3-[[N-(1-pyrrolin-2-yl)anilino)methyl] indole hydrochloride, 2.6 g., m.p. 163.5°–166.5° C. (corr.)

Analysis. Calc'd. for $C_{19}H_{19}N_3 \cdot HCl$ (percent): C,70.03; H,6.19; N,12.90; Cl,10.88. Found (percent): C,70.03; H,6.12; N,12.70; Cl,10.62.

Infrared (0.5% KBr Cm$^{-1}$): 3180, 1670, 1600, 1480, 1450, 1320, 750, 700.

NMR $\delta$ (ppm) (D$_2$O,HDO-4.70 ref.): 3.65 (m,2H); 3.17 (m,2H); 4.86 (s,2H).

EXAMPLE 36

3-[[N-(5-methyl-1-pyrrolin-2-yl)-p-anisidino]methyl]indole hydrochloride

Phosphorus oxychloride (3.06 g., 0.02 mole) in 10 ml. of 1,2-dichloroethane is added dropwise in 20 min. to a solution of 3-(p-anisidinomethyl)indole (5.04 g., 0.02 mole), 5-methyl-2-pyrrolidinone (1.98 g., 0.02 mole) and triethylamine (2.02 g., 0.02 mole) held at a temperature of about 3° C. When the addition is complete, the mixture is stirred at 3 to 4° C. for 5 hr. and then filtered to provide 2.4 g. solid which is crystallized from water affording 1.02 g., m.p. 184°–187° C. This fraction is combined with an additional 1.81 g. fraction obtained as hereinabove described and crystallized from ethanol to furnish analytically pure 3-[[N-(5-methyl-1-pyrrolin-2-yl)-p-anisidino]methyl]indole hydrochloride, m.p. 181.5°–183° C. (corr.)

Analysis. Calc'd. for $C_{21}H_{23}N_3 \cdot HCl$ (percent): C,68.19; H,6.54; N,11.36; Cl,9.58. Found (percent): C,68.03; H,6.60; N,11.29; Cl,9.58.

Infrared (0.5% KBr Cm$^{-1}$): 3160, 1660, 1510, 1450, 1300, 1250, 750.

NMR $\delta$ (ppm) (D$_2$O, HDO-4.70 ref.): 3.60, 3.62 (ss,3H total); 1.20,1.39(d d,3H total, 6.5Hz); 4.85,4.92(ss,2H total)

EXAMPLE 37

3-[[N-(5-methyl-1-pyrrolin-2-yl)anilino]methyl]indole hydrochloride

Phosphorus oxychloride (7.67 g., 0.05 mole), 3-(anilinomethyl)indole (11.1 g., 0.05 mole), 5-methyl-2-pyrrolidinone (4.96 g., 0.05 mole) and triethylamine (5.06 g., 0.05 mole) in 100 ml. of 1,2-dichloroethane reacted according to the method of Example 35 provides a total yield of 7.55 g. of the product as the free base. A 5.5 g. sample of the free base is converted to the hydrochloride salt in the usual manner in ethanol with ethanolic hydrogen chloride. Addition of ether to the acidified ethanolic solution affords on standing 3.4 g. of analytically pure 3-[[N-(5-methyl-1-pyrrolin-2-yl)anilino]methyl]indole hydrochloride, m.p. 172.5°–174° C. (corr.)

Analysis. Calc'd. for $C_{20}H_{21}N_3 \cdot HCl$ (percent): C,70.68; H,6.53; N,12.36; Cl,10.43: Found (percent): C,70.41; H,6.56; N,12.66; Cl,10.25.

Infrared (0.5% KBr Cm$^{-1}$): 3160, 1650, 1590, 1490, 1450, 740, 700.

NMR $\delta$ (ppm) (D$_2$O, HDO-4.70 ref.): 1.10,1.35 (dd, 3H total,6.4Hz); 4.82,4.95 (ss,2H total).

EXAMPLE 38

3-[(N-[1-pyrrolin-2-yl]anilino)methyl]-1-methylindole hydrochloride

Phosphorus oxychloride (4.6 g., 0.03 mole), 3-(anilinomethyl)-1-methylindole (7.1 g., 0.03 mole), 2-pyrrolidinone (2.55 g., 0.03 mole) and triethylamine (3.04 g., 0.03 mole) in 75 ml. of 1,2-dichloroethane are reacted according to the procedure of Example 35. The reaction mixture is quenched in 100 ml. of 10% sodium hydroxide and ice and the organic layer separated therefrom. The organic layer is extracted first with 100 ml. of 1.5 N hydrochloricc acid and then 100 ml. of water. The combined extracts are washed with ether, made basic with sodium hydroxide, extracted with ether and the ethereal extract dried over magnesium sulfate and concentrated under reduced pressure to provide 6.6 g. of a residual oil which on trituration with ether forms a solid. Crystallization from Skellysolve B yields 4.2 g. of 3-[(N-[1-pyrrolin-2-yl]anilino)methyl]-1-methylindole as the free base, m.p. 95°–97° C. A 2.2 g. sample of the free base is taken up in ethanol and acidified with ethanolic hydrogen chloride and the solution concentrated under reduced pressure. The residue thus obtained is refluxed with benzene permitting the benzene solution to slowly distill. On standing, 1.7 g. of analytically pure 3-[(N-[1-pyrrolin-2-yl]anilino)methyl]-1-methylindole hydrochloride, m.p. 150.5°–154.5° C. (dec.) (corr.) is obtained.

Analysis. Calc'd. for $C_{20}H_{21}N_3 \cdot HCl$ (percent): C,70.68; H,6.53; N,12.36; Cl,10.43. Found (percent): C,70.66; H,6.69; N,12.20; Cl,10.44.

Infrared (0.5% KBr Cm$^{-1}$): 3000, 1650, 1590, 1500, 1320, 750, 710.

NMR δ (ppm) CDCl$_3$, tetramethylsilane ref.): 2.39 (t,2H,6.7Hz); 1.79 (p,2H); 3.25 (t,2H,6.8Hz); 4.81 (s,2H); 3.78 (s,3H).

EXAMPLE 39

3-[[N-(5,5-dimethyl-1-pyrrolin-2-yl)anilino]methyl]indole hydrochloride

Phosphorus oxychloride (7.67 g., 0.05 mole) in 20 ml. of 1,2-dichloroethane is added rapidly to 3-(anilinomethyl)indole (11.1 g., 0.05 mole), 5,5-dimethyl-2-pyrrolidinone (5.66 g., 0.05 mole) and triethylamine (5.06 g., 0.05 mole) in 80 ml. of 1,2-dichloroethane at ice bath temperature. After stirring the mixture for about 15 min., the ice bath is removed and stirring continued at room temperature for 16 hr. Workup of the reaction mixture is as follows. The mixture is quenched in 100 ml. of 10% sodium hydroxide and crushed ice and the organic layer separated. The organic layer is extracted with 100 ml. of 1.5 N hydrochloric acid and then with 100 ml. of water. After washing the combined extracts with ether and making basic with 10% sodium hydroxide, a solid precipitates which is collected and crystallized from ethyl acetate, yield 3.2 g., m.p. 124°–126° C. of free base product. The dichloroethane fraction is dried over magnesium sulfate and concentrated in vacuum and the residue (10.4 g.) triturated with water and filtered. The aqueous filtrate is made basic with sodium hydroxide providing a second free base fraction, yield 3.1 g., m.p. 125°–127° C. The two free base fractions are combined, dissolved in ethanol and treated with ethanolic hydrogen chloride affording 3.7 g., m.p. 185°–185.5° C. (dec.) (corr.) of analytically pure 3-[(N-(5,5-dimethyl-1-pyrrolin-2-yl)anilino]methyl]indole hydrochloride.

Analysis. Calc'd. for $C_{21}H_{23}N_3 \cdot HCl$ (percent): C,71.27; H,6.84; N,11.87; Cl,10.02. Found (percent): C,71.45; H,6.81; N,11.84; Cl,9.93.

Infrared (0.5% KBr Cm$^{-1}$): 3120, 1650, 1590, 1500, 1460, 760, 710.

NMR δ (ppm) (D$_2$O, HDO-4.70 ref.): 1.28 (s,6H); 4.87 (s,2H).

EXAMPLE 40

3-[[N-(5,5-dimethyl-1-pyrrolin-2-yl)-p-anisidino]methyl]indole hydrochloride

Phosphorus oxychloride (1.53 g., 0.01 mole), 3-(p-anisidinomethyl)indole, (2.52 g., 0.01 mole), 5,5-dimethyl-2-pyrrolidinone (1.13 g., 0.01 mole), and triethylamine (1.01 g., 0.01 mole) in 50 ml. of 1,2-dichloroethane is reacted according to the procedure of Example 36. After standing for 6 hr. at ice bath temperature, the reaction mixture is filtered affording the crude hydrochloride salt (1.45 g.) of the product, m.p. 188°–191° C. The dichloroethane filtrate is made basic with 10% sodium hydroxide, separated, dried over magnesium sulfate, acidified with ethanolic hydrogen chloride, and concentrated under reduced pressure. Trituration of the residue thus obtained with acetone yields a second crop of the hydrochloride, (0.76 g.), m.p. 191°–194° C. The hydrochloride fractions are combined and converted to the free base (m.p. 83°–85° C.) in the usual manner by dissolving in water and making basic with sodium hydroxide followed by extraction with ether. The hydrochloride salt is reprepared by taking the free base up in ethanol and acidifying with ethanolic hydrogen chloride to provide analytically pure 3-[[N-(5,5-dimethyl-1-pyrrolin-2-yl)-p-anisidino]methyl]indole hydrochloride, m.p. 188.5°–190.5° C. (dec) (corr.)

Analysis. Calc'd. for $C_{22}H_{25}N_3 \cdot HCl$ (percent): C,68.82; H,6.83; N,10.95; Cl,9.23. Found (percent): C,68.69; H,6.77; N,10.79; Cl,9.36.

Infrared (0.5% KBR Cm$^{-1}$): 2980, 1650, 1510, 1450, 1260, 1180, 1040, 750.

NMR δ (ppm) (DMSO-d$_6$, tetramethylsilone ref.): 3.72 (s,3H); 1.50 (s,6H); 5.27 (s,2H); 11.33 (broad s,1H).

EXAMPLE 41

3-[[4-methoxy-2-methyl-N-(1-pyrrolin-2-yl)anilino]methyl]indole hydrochloride

Phosphorus oxychloride (7.7 g., 0.05 mole) in 20 ml. of 1,2-dichloroethane is added rapidly to a stirred mixture of N-(3-indolylmethyl)-4-methoxy-2-methylaniline (13.3 g., 0.05 mole), 2-pyrrolidinone (4.3 g., 0.05 mole) and triethylamine (5.1 g., 0.05 mole) in 120 ml. 1,2-dichloroethane at ice bath temperature. After the addition is complete, the cooling bath is removed, the mixture stirred at room temperature for a 16 hr. period, and then quenched in 200 g. of crushed ice and made basic with 40% aqueous sodium hydroxide. Extraction of the organic layer with 10% aqueous hydrochloric acid, washing the aqueous extract with ether and then making basic with aqueous sodium hydroxide provides a gummy substance which is collected. This material is extracted with ether, the ethereal extract dried over magnesium sulfate and concentrated provides a residue which is dissolved in 20 ml. of ethanol and acidified with ethanolic hydrogen chloride. Dilution of the acidified solution with ether yields 2.34 g. of analytically pure 3-[[4-methoxy-2-methyl-N-(1-pyrrolin-2-yl)anilino]methyl]indole hydrochloride, m.p. 178°–180° C. (corr.)

Analysis. Calc'd for $C_{21}H_{23}N_3 \cdot HCl$ (percent): C,68.18; H,6.53; Cl,9.65; N,11.35. Found (percent): C,67.92; H,6.46; Cl,9.72; N,11.18.

Infrared (0.5% KBr Cm$^{-1}$): 3450, 3200, 1660, 1510, 1460, 1320, 1240, 750.

NMR δ (ppm) (DMSO-d$_6$, tetramethylsilene ref.): 3.73 (s,3H); 1.89 (s,3H); 5.23 (s,2H).

EXAMPLES 42–53

Additional exemplification of N-phenylamidines characterized by Formula I wherein Z is $R^4$, $R^5$-indole are prepared according to the procedures of Examples 34 to 41 by reacting the appropriately substituted anilinoindole, the carboxamid reactant and phosphorus oxchloride in 1,2-dichloroethane solution employing triethylamine are listed in Table IV. The anilinoindole reactants are obtained according to methods well known to those skilled in the art. For example, the Shiff base, N-(3-methylene-1-methylindole)aniline is obtained by condensation of 1-methylindole-3-carboxaldehyde with aniline in refluxing toluene. Reduction of the Schiff base with sodium borohydride affords the 3-(anilinomethyl)-1-methylindole intermediate.

TABLE IV
ADDITIONAL N-PHENYL AMIDINES

| EXAMPLE NUMBER | X | Y | Alk | $R^4$ | $R^5$ | A |
|---|---|---|---|---|---|---|
| 42 | H | H | —$CH_2$— | H | Br |  |
| Reactants: | 3-(anilinomethyl)-5-bromoindole and 2-pyrrolidinone | | | | | |
| 43 | p-$CH_3$O | H | —$CH_2$— | H | Br |  |
| Reactants: | 3-(p-methoxyanilinomethyl)-5-bromoindole and 2-pyrrolidinone | | | | | |
| 44 | H | H | —$CH_2$— | H | $CH_3$O |  |
| Reactants: | 3-(anilinomethyl)-5-methoxyindole and 2-pyrrolidinone | | | | | |
| 45 | p-$CH_3$O | H | —$CH_2$— | H | $CH_3$O |  |
| Reactants: | 3-(p-methoxyanilinomethyl)-5-methoxyindole and 2-pyrrolidinone | | | | | |
| 46 | H | H | —$CH_2$— | —$CH(CH_3)_2$ | H |  |
| Reactants: | 3-(anilinomethyl)-1-isopropylindole and 2-pyrrolidinone | | | | | |
| 47 | m-$CH_3$ | p-$CH_3$ | —$CH_2$— | H | H |  |
| Reactants: | 3-(m,p-dimethylanilinomethyl)indole and 2-pyrrolidinone | | | | | |
| 48 | H | H | —$CH_2$— | H | H |  |
| Reactants: | 3-(anilinomethyl)indole and 3-ketomorpholine | | | | | |
| 49 | H | H | —$CH_2$— | H | H |  |
| Reactants: | 3-(anilinomethyl)indole and 3-ketothiomorpholine | | | | | |
| 50 | H | H | —$CH_2$— | H | H | —CH=N—$CH_3$ |
| Reactants: | 3-(anilinomethyl)indole and N-methylformamide | | | | | |
| 51 | H | H | —$CH_2$— | H | H | —CH=N—$CH(CH_3)_2$ |
| Reactants: | 3-(anilinomethyl)indole and N-isopropylformamide | | | | | |
| 52 | H | H | —$CH_2$— | H | H | —CH=N—$C(CH_3)_3$ |
| Reactants: | 3-(anilinomethyl)indole and N-tert.-butylformamide | | | | | |
| 53 | H | H | —$CH_2CH_2$— | H | H |  |
| Reactants: | 3-(anilinoethyl)indole and | | | | | |

TABLE IV-continued
ADDITIONAL N-PHENYL AMIDINES

| EXAMPLE NUMBER | X | Y | Alk | R⁴ | R⁵ | A |
|---|---|---|---|---|---|---|
| | | | | | | 2-pyrrolidinone |

EXAMPLE 54

3-[[2-(p-methoxyphenylimino)-1-pyrrolidinyl]methyl]-indole hydrochloride

The mother liquors of the various fractions obtained from the purification of 3-[(N-[1-pyrrolin-2-yl]-p-anisidino)-methyl]indole hydrochloride in Example 34 are combined and concentrated under reduced pressure. Water and ether are added to the residue thus obtained and the mixture basified with aqueous sodium hydroxide. The ether layer is separated, dried over magnesium sulfate, and concentrated yielding basic material which is taken up in ethanol, refluxed for about 2 hr., concentrated and the residue then crystallized from ethyl acetate. The hydrochloride salt of this material is prepared in the usual manner in ethanol with ethanolic hydrogen chloride. Addition of ether to the acidified mixture precipitates the solid hydrochloride salt which is taken up in ethanol, treated with decolorizing charcoal and diluted with ether to yield 1.23 g. of analytically pure 3-[[2-(p-methoxyphenylimino)-1-pyrrolidinyl]methyl]-indole hydrochloride, m.p. 177°-178.5° C. (corr.), characterized by the formula:

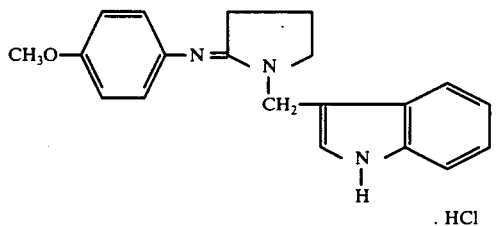

Analysis. Calc'd. for $C_{20}H_{21}N_3 \cdot HCl$ (percent): C,67.50; H,6.23; N,11.81; Cl,9.96. Found (percent): C,67.20; H,6.36; N,11.59; Cl,9.87.

Infrared (0.5% KBr Cm⁻¹): 3160, 1660, 1510, 1440, 1300, 1240, 1030, 750.

NMR δ (ppm) (D₂O, HDO-470 ref.): 3.91 (s,3H); 4.98 (s,2H); 3.69 (m,2H).

EXAMPLE 55

3-[(2-phenylamino-1-pyrrolidinyl)methyl]indole

Phosphorus oxychloride (7.67 g., 0.05 mole), 3-(anilinomethyl)indole (11.1 g., 0.05 mole), 2-pyrrolidinone (4.26 g., 0.05 mole) and triethylamine (5.06 g., 0.05 mole) in 100 ml. of 1,2-dichloroethane reacted according to the procedure of Example 35 provide a total of 6.4 g. of crude 3-[[N-(1-pyrrolin-2-yl)anilino]methyl]indole as the free base. The crude free base is taken up in ethanol and refluxed for 6 hr., treated with decolorizing charcoal and filtered. Concentration of the ethanol filtrate to about 20 ml. provides on standing a solid which crystallized from ethanol affords 2.75 g. of analytically pure 3-[(2-phenylimino-1-pyrrolidinyl)methyl]indole, m.p. 150°-151° C. (corr.), characterized by the formula:

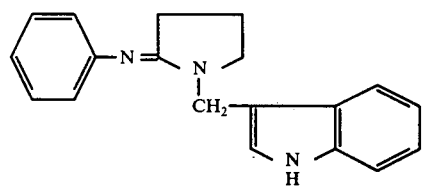

Analysis. Calc'd. for $C_{19}H_{19}N_3$ (percent): C,79.14; H,6.29; N,14.57. Found (percent): C,79.19; H,6.21; N,14.41.

Infrared (0.5% KBr Cm⁻¹): 3400, 3060, 1640, 1600, 1470, 1290, 1260, 1240, 760.

NMR δ (ppm) (CDCL₃, tetramethylsilane ref.): 2.37 (t,2H,6.6Hz); 1.74 (p,2H); 3.17 (t,2H,6.6Hz); 4.77 (s,2H); 8.62 (broad s,1H).

EXAMPLE 56

3-[[2-[(p-methoxyphenyl)imino]-5-methyl-1-pyrrolidinyl]methyl]indole hydrochloride An aqueous solution of 3-[[N-(5-methyl-1-pyrrolin-2-yl)-p-anisidino]methyl]indole hydrochloride (4.75 g.) obtained according to Example 36 is covered with ether and the mixture made basic. After separating the ether layer and drying over magnesium sulfate, the ethereal extract is concentrated to provide a residue which is crystallized from ethanol yielding 2.7 g. of 3-[[2-[p-methoxyphenyl)imino]-5-methyl-1-pyrrolidinyl]methyl]indole free base. The free base is suspended in ethanol and acidified with ethanolic hydrogen chloride. Addition of ether to the ethanolic solution yields analytically pure 3-[[2-[(p-methoxyphenyl)imino]-5-methyl-1-pyrrolidinyl]methyl]indole hydrochloride, m.p. 197°-198° C. (dec.) (corr.), characterized by the formula:

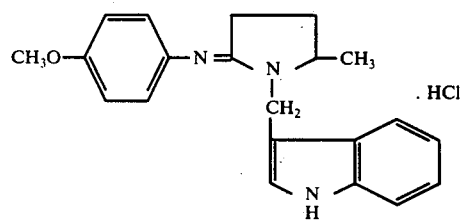

Analysis. Calc'd. for $C_{21}H_{23}N_3 \cdot HCl$ (percent): C,68.19; H,6.54; N,11.36; Cl,9.58. Found (percent): C,68.47; H,6.52; N,11.37; Cl,9.20.

Infrared (0.5% KBr cm⁻¹): 3160, 1650, 1520, 1460, 1300, 1250, 750.

NMR δ (ppm) (CDCl₃, tetramethylsilane ref.): 3.76 (s,3H); 4.22,6.00(dd,2H,15.4Hz); 10.92 (broad s,1H); 3.67 (m,2H); 1.85 (m,2H); 3.65 (m,1H); 1.15 (d,3H,6.4Hz).

EXAMPLE 57

3-[(5-methyl-2-phenylimino-1-pyrrolidinyl)methyl]indole

The 6.1 g. sample of 3-[[N-(5-methyl-1-pyrrolin-2-yl)anilino]methyl]indole as a free base, m.p. 88°–92° C., is heated at 180° C. in an oil bath for 2 hr. under nitrogen. The cooled pyrrolized product is extracted with five 100 ml. portions of Skellysolve B. On standing, the Skellysolve B extract yields 3.54 g. of a crystalline product m.p. 130°–134° C. Crystallization of this material from benzene-cyclohexane provides analytically pure 3-[(5-methyl-2-phenylimino-1-pyrrolidinyl)methyl]indole, m.p. 136.5°–141° C. (corr.), characterized by the formula:

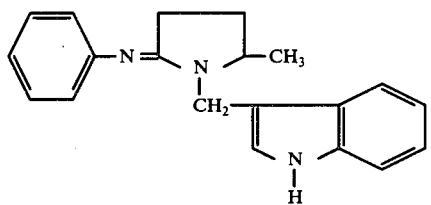

Analysis. Calc'd. for C₂₀H₂₁N₃ (percent): C,79.17; H,6.98; N,13.85. Found (percent): C,79.17; H,7.06; N,13.78.

Infrared (0.5% KBr Cm⁻¹): 3400, 3160, 3060, 2980, 1630, 1590, 1460, 1420, 790, 750, 700.

NMR δ (ppm) (CDCl₃, tetramethylsilane ref.): 4.19, 5.43 (dd,2H,15.2Hz); 8.70 (broad s, 1H); 1.15 (d,3H,6.2Hz); 3.37 (sextet,1H).

EXAMPLE 58

Preparation of additional iminopyrrolidinylindoles.

According to the procedure described above in Examples 54–57, preferably that of Example 55, the following N-phenylamidines:

3-[(N-[1-pyrrolin-2-yl]anilino)methyl]-1-methylindole,
3-[(N-[5,5-dimethyl-1-pyrrolin-2-yl]anilino)methyl]indole,
3-[[N-(5,5-dimethyl-1-pyrrolin-2-yl)-p-anisidino]methyl]indole,
3-[[4-methoxy-2-methyl-N-(1-pyrrolin-2-yl)anilino]methyl]indole,
3-[[N-(1-pyrrolin-2-yl)anilino]methyl]-1-benzylindole, can be rearranged on heating to respectively produce:
3-[(2-phenylimino-1-pyrrolidinyl)methyl]-1-methylindole,
3-[(5,5-dimethyl-2-phenylimino-1-pyrrolidinyl)methyl]indole,
3-[[2-[(p-methoxyphenyl)imino]-5,5-dimethyl-1-pyrrolidinyl]methyl]indole,
3-[[2-(o-methyl-p-methoxyphenylimino)-1-pyrrolidinyl]methyl]indole,
3-[(2-phenylimino-1-pyrrolidinyl)methyl]-1-benzylindole.

EXAMPLE 59

5-Bromo-3-[(2-[p-methoxyphenylimino]-1-pyrrolidinyl)methyl]indole hydrochloride

Reaction of equimolar amounts of phosphorus oxychloride, 3-(p-anisidinomethyl)-5-bromoindole, 2-pyrrolidinone and triethylamine in 1,2-dichloroethane according to the procedure of Example 35 provides 5-bromo-3-[(N-[1-pyrrolin-2-yl]-p-anisidino)methyl]indole. Acidification of the free base with ethanolic hydrogen chloride provides 5-bromo-3-[(N-[1-pyrrolin-2-yl]-p-anisidino)methyl]indole hydrochloride, m.p. 205.5°–207.5° C. (corr.).

5-Bromo-3-[(N-[1-pyrrolin-2-yl]-p-anisidino)methyl]indole free base is taken up in chloroform, the chloroform solution permitted to stand for two days and the solvent removed under reduced pressure. The residue thus obtained is taken up in absolute ethanol, acidified with ethanolic hydrogen chloride and the acidified ethanolic solution treated with decolorizing charcoal and filtered. The filtrate diluted with ether provides 5-bromo-3-[(2-[-p-methoxyphenylimino]-1-pyrrolidinyl)-methyl]indole hydrochloride, m.p. 214.5°–215.5° C. (corr.), characterized by the formula:

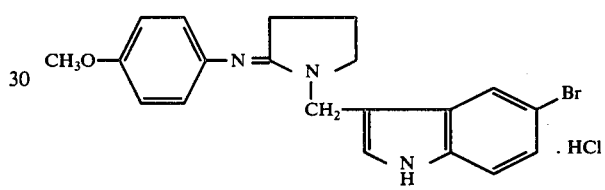

Analysis. Calcd. for C₂₀H₂₀BrN₃O·HCl: C, 55.12; H, 5.09; N, 9.64; Cl, 8.14. Found: C, 55.36; H, 4.87; N, 9.58; Cl, 8.12.

NMR δ (ppm)(DMSO-d₆, tetramethylsilane reference): 1.92 (m, 2H), 2.84 (t, 7.5 Hz, 2H), 3.61 (t, 7.4 Hz, 2H), 3.75 (s, 3H), 5.14 (s, 2H), 7.37 (m,8H), 11.2 (bs, 1H), 11.5 (bs, 1H).

EXAMPLE 60

3,4,5,6,7,8-Hexahydro-2-(N-phenylphenethylamino)-azocine hydrochloride hemihydrate Phosphorus oxychloride (6.13 g., 0.04 mole) is added in one portion to a stirred mixture of 2-azacyclooctanone (5.1 g., 0.04 mole) and N-phenylphenethylamine (7.9 g., 0.04 mole) in 100 ml. of 1,2-dichloroethane. The mixture is stirred for 16 hr., poured into crushed ice and made basic with 10 N potassium hydroxide. The 1,2-dichloroethane layer is separated, washed with 100 ml. of 1.5 N hydrochloric acid and then with a 100 ml. portion of water. After drying over magnesium sulfate, the 1,2-dichloroethane fraction is concentrated under reduced pressure to provide 10.6 g. of residue which is stirred with water, extracted with ether and then made basic with potassium hydroxide and again extracted with ether. The ethereal extract of the basic mixture is dried (magnesium sulfate) and concentrated under reduced pressure. Distillation of the resulting residue yields 3.5 g., b.p. 152°–170° C./0.15 mm. Hg. of the azocine product free base. The free base is converted to the hydrochloride in ethanol by the addition of ethanolic hydrogen chloride and is recovered by addition of ether affording analytically pure 3,4,5,6,7,8-hexahydro- 2-(N-phenylphenethylamino)azocine hydrochloride hemihydrate, m.p. 165°–168° C. (corr.).

Analysis. Calcd. for $C_{21}H_{26}N_2 \cdot HCl \cdot 1/2H_2O$: C, 71.67; H, 8.03; N, 7.96; Cl, 10.07. Found: C, 71.61; H, 8.05; N, 7.96; Cl, 9.62.

NMR δ(ppm)(CDCl₃, tetramethylsilane reference): 1.48 (m, 6H), 1.86 (m, 2H), 2.37 (m, 2H), 3.05 (t, 7.0 Hz, 2H), 3.72 (m, 2H), 4.47 (t, 7.0 Hz, 2H), 6.90 (m, 2H), 7.28 (m, 8H), 11.2 (bs, 1H).

EXAMPLE 61

4,5,6,7,8,9-Hexahydro-2-(N-phenylphenethylamino)-3H-azonine Hydrochloride

Reaction of equimolar amounts of 2-azocyclononanone, N-phenylphenethylamine and phosphorus oxychloride in 1,2-dichloroethane according to the procedure of Example 60 provides the azonine free base in 73% yield, b.p. 170°–175° C./0.1 mm. Hg. The free base is converted to the hydrochloride salt in ethanol with ethanolic hydrogen chloride. Addition of ether to the acidified ethanolic solution affords analytically pure 4,5,6,7,8,9-hexahydro-2-(N-phenylphenethylamino)-3H-azonine hydrochloride, m.p. 141°–143.5° C. (corr.).

Analysis. Calcd. for $C_{22}H_{28}N_2 \cdot HCl$ (percent): C, 74.02; H, 8.19; N, 7.85; Cl, 9.94. Found (percent): C, 74.17; H, 8.36; N, 7.68; Cl, 10.09.

NMR δ (ppm)(CDCl₃, tetramethysilane reference): 1.49 (m, 8H), 1.92 (m, 2H), 2.38 (m, 2H), 3.09 (t, 7.0 Hz, 2H), 3.75 (m, 2H), 4.51 (t, 7.0 Hz, 2H), 6.89 (m, 2H), 7.28 (m, 8H), 11.0 (bs, 1H).

EXAMPLE 62

2-(N-Phenylphenethylamino)-1-aza-1-cyclotridecene hydrochloride

Reaction of equimolar amounts of 2-azocyclotridecanone with N-phenylphenethylamine and phosphorus oxychloride in 1,2-dichloroethane according to the procedure of Example 60 affords 2-(N-phenylphenethylamino)-1-aza-1-cyclotridecene hydrochloride, m.p. 174°–177° C. (corr.).

Analysis. Calcd. for $C_{26}H_{36}N_2 \cdot HCl$ (percent): C, 75.60; H, 9.03; N, 6.78; Cl, 8.59. Found (percent): C, 75.61; H, 9.27; N, 7.01; Cl, 8.48.

NMR δ (ppm)(CDCl₃, tetramethylsilane reference): 1.28 (m, 16H); 2.00 (m, 4H), 3.07 (t, 7.0 Hz, 2H), 3.50 (m, 2H), 4.47 (t, 7.0 Hz, 2H), 6.80 (m, 2H), 7.23 (m, 8H), 11.1 (bs, 1H).

EXAMPLE 63

Reaction of ε-caprolactam, 2-azacyclooctanone, 2-azacyclononanone, and 2-azacyclotridecanone respectively with phosphorus oxychloride and N-phenylbenzylamine in 1,2-dichloroethane according to the procedure of Example 60 provides the corresponding N-phenylamidines:

3,4,5,6-tetrahydro-7-[(N-phenyl)benzylamino]-2H-azepine,
3,4,5,6,7,8-hexahydro-2-(N-phenylbenzylamino)azocine,
4,5,6,7,8,9-hexahydro-2-(N-phenylbenzylamino)-3H-azonine,
2-(N-phenylbenzylamino)-1-aza-1-cyclotridecene.

What is claimed is:

1. A compound selected from the group consisting of N-phenyl amidines of Formula I

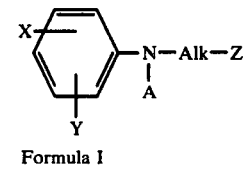

Formula I and pharmaceutically acceptable acid addition salts of compounds of Formula I wherein Alk is alkylene having 1 or 2 carbon atoms;
X and Y are independently selected from the group consisting of hydrogen, halogen, trifluoromethyl, lower alkoxy of from 1 to 4 carbon atoms inclusive, lower alkyl of from 1 to 4 carbon atoms inclusive;
Z is phenyl; and
A is —CH=N—R¹
wherein
R¹ is lower alkyl of from 1 to 4 carbon atoms inclusive.

2. The compound of the group defined in claim 1 which is N'-isopropyl-N-phenyl-N-(1-phenylethyl)formamidine.

3. The compound of the group defined in claim 1 which is N-benzyl-N'-tert.-butyl-N-phenylformamidine hydrochloride.

4. The compound of the group defined in claim 1 which is N-benzyl-N'-tert.-butyl-N-phenylformamidine.

5. The compound of the group defined in claim 1 which is N'-tert.-butyl-N-phenethyl-N-phenylformamidine hydrochloride.

6. The compound of the group defined in claim 1 which is N'-tert.-butyl-N-phenethyl-N-phenylformamidine.

* * * * *